US006420552B1

(12) United States Patent
Srivastava et al.

(10) Patent No.: US 6,420,552 B1
(45) Date of Patent: Jul. 16, 2002

(54) SYNTHESES OF 4-ALKYL CHROMOGENIC GLYCOSIDES AND 7-ALKYL CHROMOGENIC GLYCOSIDES OF N-ACETYLNEURAMINIC ACIDS

(75) Inventors: Om Srivastava; Geeta Srivastava; Minghui Du; Ole Hingsgaul; David R. Bundle, all of Edmonton (CA)

(73) Assignee: Zymetx, Inc., Oklahoma City, OK (US)

( * ) Notice: Subject to any disclaimer, the term of this patent is extended or adjusted under 35 U.S.C. 154(b) by 0 days.

(21) Appl. No.: 09/650,162

(22) Filed: Aug. 29, 2000

Related U.S. Application Data (60) Provisional application No. 60/153,444, filed on Sep. 10, 1999.

(51) Int. Cl.$^7$ .................................................. C07H 1/00
(52) U.S. Cl. .................... 536/55.3; 536/18.5; 536/18.6; 536/53
(58) Field of Search .............................. 536/55.3, 18.5, 536/18.6, 53

(56) References Cited

U.S. PATENT DOCUMENTS

| | | | |
|---|---|---|---|
| 3,950,322 A | 4/1976 | Thomas et al. | 260/210 R |
| 4,632,901 A | 12/1986 | Valkirs et al. | 435/5 |
| 4,772,553 A | 9/1988 | Fujii et al. | 435/13 |
| 4,810,636 A | 3/1989 | Corey | 435/14 |
| 4,877,727 A | 10/1989 | Miike et al. | 435/24 |
| 5,081,017 A | 1/1992 | Longoria | 435/30 |
| 5,252,458 A | 10/1993 | Liav et al. | 435/5 |
| 5,489,675 A | 2/1996 | Sabsesan | 536/17.2 |
| 5,556,963 A | 9/1996 | Liav | 436/55.3 |
| 5,663,055 A | 9/1997 | Turner et al. | 435/18 |
| 5,719,020 A | 2/1998 | Liav et al. | 435/5 |

FOREIGN PATENT DOCUMENTS

| | | | |
|---|---|---|---|
| AU | 71647/91 | 12/1990 | |
| EP | 91902414.1 | 12/1990 | |
| JP | 3-502946 | 12/1990 | |
| WO | WO 91/09972 | 7/1991 | ............ C12Q/1/34 |
| WO | WO 91/16320 | 10/1991 | ......... C07D/309/30 |
| WO | WO 92/06691 | 4/1992 | ......... C07D/309/28 |
| WO | WO 96/04291 | 2/1996 | ........... C07H/15/04 |

OTHER PUBLICATIONS

Jean–Marie Beau et al., "Synthèse De L'Acide 5– Acétamido–Didésoxy–4–O–Méthyl–N–Acétylneuraminique). Partie II", *Carbohydrate Research*, 67 (1978) pp. 65–77.

Jean–Marie Beau et al., "Synthèse De L'Acide 4–O–Méthyl–N–Acétylneuraminique. Partie I. Acétonation Du 3–Acétamido–3–Désoxy–D–glycéro–D–galacto–Heptose Diéthyldithioacétal", *Carbohydrate Research*, 65 (1978) pp. 1–10.

von Richard Kuhn et al., "ÜberfÜhrung Von 2–Amino–2–Desoxy–Hexosen in 3–Amino–3–Desoxy–Hexosen Und – Pentosen", Bd. 636 (1960) pp. 164–173.

E. Zbiral et al., "Synthesis of the 4–Methylumbelliferyl 2α–Glycosides of 7–Epi, 8–Epi, and 7,8–Bis(epi)– N–acetylneuraminic Acids, as well as of 7–Deoxy–, 8–Deoxy–, 9–Deoxy–, and 4,7–Dideoxy–N_acetylneuraminic Acids and Their Behaviour Towards Sialidase from *Vibrio cholerae*", *Liebigs Ann. Chem.*, (1989), pp. 519–526.

Hagedorn et al., "Synthesis and Biological Properties of N–Acetyl–4–deoxy–D–neuraminic Acid", *Helvetica Chimica Acta*, vol. 69 (1986) pp. 2127–2133.

Baumberger et al., "4–Methylumbelliferyl 5–Acetamido–3, 4,5–trideoxy–α–D–manno–2–nonulopyranosidonic Acid: Synthesis and Resistance to Bacterial Sialidases", *Helvetica Chimica Acta*, vol. 69, (1986), pp. 1927–1935.

Warner et al., "Synthesis of 2'–(4–Methylembelliferyl)–α–D–N–acetylneuraminic Acid and Detection of Skin Fibroblast Neuraminidase in Normal Humans and in Sialidosis", *Biochemistry*, vol. 18, No. 13, (1979), pp. 2783–2787.

Kim et al., "Enzymes in Carbohydrate Synthesis: N–Acetylneuraminic Acid Aldolase Catalyzed Reactions and Preparation of N–Acetyl–2–deoxy–D–neuraminic Acid Derivatives", *J. Am. Chem. Soc.*, (1988) 110, pp. 6481–6486.

Baumberger et al., "4–Methylembelliferyl 5–Acetamido–3, 4,5–trideoxy–α–D–manno–2–nonulopyranosidonic Acid: Synthesis and Resistance to Bacterial Sialidases", *Helvetica Chimica Acta*, vol. 69 (1986), pp. 1927–1935.

Santer et al., "A Rapid Assay for Neuraminidase—The Detection of Two Differences in Activity Associated With Virus Transformation", *Biochimica et Biophysica Acta*, 523 (1978) pp. 435–442.

(List continued on next page.)

*Primary Examiner*—Elli Peselev
(74) *Attorney, Agent, or Firm*—Fitch, Even, Tabin & Flannery (57) ABSTRACT

The present invention provides improved method of preparing a 4-O-alkyl chromogenic ketoside of N-acetylneuraminic acid (Neu5Ac) and a 7-O-alkyl chromogenic ketoside of N-acetylneuraminic acid (Neu5Ac) for use in the selective detection of various influenza viruses and parainfluenza viruses. The ketosides are substrates that are selectively cleaved by a neuraminidase on the virus to be detected, but not by neuraminidases found on other viruses or on bacteria, or on the cells of the host. The syntheses are efficient and provide large quantities of the ketosides for commercial development. The synthesis includes a step of alkylating the 4- or 7-hydroxyl groups of a protected alkyl ester alkyl ketoside derivative of Neu5Ac by processes that include contacting the derivative with a composition comprising an alkyl halide to form a 4- or a 7-O-alkyl protected alkyl ester alkyl ketoside derivative of Neu5Ac. The syntheses alternatively include protecting the 8- and 9-hydroxyl groups of an alkyl ester alkyl ketoside derivative of Neu5Ac by forming an 8,9-ketal or an 8,9-epoxide protected alkyl ester alkyl ketoside derivative of Neu5Ac.

33 Claims, 2 Drawing Sheets

OTHER PUBLICATIONS

Cabezas et al., "Neuraminidase From Influenza Virus A (H3N2)—Specificity Towards Several Substrates and Procedure of Activity Determination", *Biochimica et Biophysica Acta*, 616 (1980) pp. 228–238.

Abstract #27461—Katsuhiro et al., "Fluorometric Measurement of Neuraminidase Activity of Influenza Viruses", *Hiroshima J. Med. Sci.*, 33(2) (1984) pp. 287–292. (Listed in *Veterinary Science*.).

Abstract #78292—Katsuhiro et al., "Enzymological heterogeneity of influenza B virus neuraminidase demonstrated by the *Science*, fluorometric assay method", *Zentralbl Bakteriol Mikrobiol Hyg Ser A*, 260(2): 273–285 (1985), pp. 273–285 (Listed in *Veterinary* Biol. Abst. (81(8) AB 1090).

Abstract #117445—Takei et al., "Enzymologically Neuraminidase (NA) activity of 10 strains of influenza A and B viruses neuraminicases", *Virus* (Tokyo) (1986) 36(1): pp. 119–124. (*Veterinary Science*.).

Baumberger et al., "Deoxy–nitrosugars", *Helvetica Chimica Acta*, vol. 69 (1986), pp. 1535–1541.

Brown et al., "Rapid Stereospecific Methylation of Alcohols and Glycols With Sodium Hydride/Methyl Iodide", *Communications*, pp. 434–435.

Gross et al., "Interaction of N–Acetyl–4–epi–D–neuraminic Acid with Key Enzymes of Sialic Acid Metabolism", *Biochemistry*, 1988, 27, pp. 4279–4283.

Liav et al., "Synthesis of 6–O–mycoloyl and 6–O–corynomycoloyl–α,αtrehalose", *Carbohydrate Research*, 125 (1984), pp. 323–328.

Pachucki et al., "Early Detection of Influenza Virus By Using a Fluorometric Assay of Infected Tissue Culture", *Journal of Clinical Microbiology*, Dec. 1988, pp. 2664–2666.

Yolken et al., "Fluorometric Assay for Measurement of Viral Neuraminidase—Application to the Rapid Detection of Influenza Virus in Nasal Wash Specimens", *The Journal of Infectious Diseases*, vol. 142, No. 4, Oct. 1980, pp. 516–523.

Beau et al., "Metabolism of 4–O–Methyl–N–acetylneuraminic Acid a Synthetic Sialic Acid", *Eur. J. Biochem.*, 106 (1980), pp. 531–540.

Zbiral et al., "Strukturelle Abwandlungen an N–Acetylneuraminsauren, 8[1] Synthese von 7–,8–,9–Desoxy– und 4,7–Didesocyneuraminsaure", *Monatshefte fur Chemie*, 199 (1988), pp. 127–141.

Myers et al., "The Synthesis of 4–Methylumbelliferyl α–Ketoside of N–Acetylneuraminic Acid and Its Use in a Fluormetric Assay of Neuraminidase", *Analytical Biochemistry*, 101, (1980) pp. 166–174.

Varki, A. et al.,"A Neuraminidase from *Streptococcus sanguis* that Can Release O–acetylated Sialec Acids", *The Journal of Biological Chemistry*, vol. 258, No. 20, Issue of Oct. 25,, pp. 12465–12471.

Kiyotani et al., *Microbiol. Immunol.* (1987) 31(11):1131–1135.

Kiyotani et al., *Zbl. Bakt. Hyg. A* (1985) 260:273–285.

Kiyotani et al., *Hiroshima Journal of Medical Sciences*, vol. 33, No. 2, pp. 287–292, Jun., 1984.

Yolken et al., *Review of Infectious Diseases* (1982) 4(1):35–68.

Yolken et al., *Clinical Chemistry* (1981) 27(9):1490–1498.

Gross et al., *Glycoconjugate Journal* (1987) 4(2):145–156.

Rothermel, J., et al., *Carbohydrate Research*, 196 (1990) pp. 29–40.

SYNTHESES OF 4-ALKYL CHROMOGENIC GLYCOSIDES AND 7-ALKYL CHROMOGENIC GLYCOSIDES OF N-ACETYLNEURAMINIC ACIDS

This application is a continuation of provisional Application No. 60/153,444 filed Sep. 10, 1999.

FIELD OF THE INVENTION

This invention relates to an improved synthesis of derivatives of N-acetylneuraminic acid monoalkylated at either the 4- or the 7-position. The synthetic procedures represent improvements and enhancements that permit obtaining large quantities of the products suitable for commercial production. These derivatives of N-acetylneuraminic acid can be used as chromogenic substrates for the detection of viral neuraminidases.

BACKGROUND OF THE INVENTION

Viral infections are a principal cause of illness due to communicable diseases that affect the public at large. Of these, influenza viruses, including types A and B, are a significant factor responsible for causing respiratory symptoms as well as systemic malaise; other respiratory viruses include parainfluenza 1, 2, 3, and 4, respiratory syncytial virus, and adenovirus. The influenza viruses undergo rapid mutation of strains, producing pathogens with varying degrees of virulence and severity of symptoms. Recently, influenza infection has been as high as the fifth leading cause of death from acute respiratory disease in the United States (Morbidity and Mortality Weekly Report, 36 (1987) 2).

Influenza virus types A, B, and C belong to the family of Orthomyxoviridae. Influenza A and B are significant pathogens in children and adults causing sever lower respiratory tract disease, whereas influenza C can cause sporadic upper respiratory tract. illness. Influenza virus is highly contagious and can affect large proportions of the population each winter. Influenza A epidemics occur every 2–3 years, whereas influenza B epidemics appear every 4–6 years. Symptoms include moderate to high fever together with chills, headache, myalgia, rhinorrhea, among others. Importantly, virus progeny are detectable 24 hours prior to the appearance of symptoms, and virus titers peak 24–48 hours after symptoms arise.

For this reason it is important to have available ways of diagnosing the presence of an influenza infection, and of distinguishing it from related viral and bacterial infections. Particularly among infants, the elderly and those having compromised or deficient immune responses, early diagnosis of influenza can lead to appropriate symptomatic treatment to minimize the risk of morbidity.

Diagnosis of viral infection, such as infection by influenza virus, may be carried out by detecting the presence of unique moieties characteristic of the virus. Virus particles typically carry distinctive antigenic components on the exterior of the virion which may be detected by specific ligand-antiligand interactions, in particular by the use of an antibody specific for a viral epitope. Such interactions rely on the law of mass action, and for this reason may have limited sensitivity. Many virus particles additionally carry specific enzymatic activities on the virion particle. Influenza viruses, parainfluenza viruses, and mumps are examples of such viruses; they are endowed with a virus-specific surface glycoprotein with neuraminidase activity as an integral part of the virion. Utilization of the enzymatic activity for diagnostic assays in such cases offers the potential for increasing the sensitivity of a detection method. For example, influenza A and B, having neuraminidase activity, are detectable in this way, whereas influenza C is not.

N-acetylneuraminic acid (sialic acid, Neu5Ac), whose structure is shown below with atoms numbered, is the terminal saccharide residue

[1]

of many complex carbohydrate side chains of cell surface glycoproteins. In this structure the C2 position is the anomeric carbon, which is characterized by being part of a hemiketal group, or the 2-ketoside moiety. The glycosidic linkage bonding Neu5Ac with the penultimate saccharide is the substrate of the neuraminidase activity of the influenza virion. The neuraminidase hydrolyzes glycosidic linkages having the a anomeric configuration, thereby cleaving Neu5Ac from the penultimate saccharide. Consequently, suitable synthetic substrates may be derivatives of Neu5Ac in 2-ketosidic a linkage with a detectable moiety. The moiety then provides a product, when the substrate is acted upon by the viral neuraminidase activity, that signals the presence and amount of influenza virus particles in a sample. Since the viral enzyme cleaves the substrate catalytically, the sensitivity of detecting the presence of the enzyme is greatly enhanced. For this reason the overall sensitivity of detection may be comparable to, and may even be improved over, that provided by antibody binding assays.

One method for detecting the presence of a virus through the reaction of an enzyme with a chromogenic substrate for the enzyme is described in U.S. Pat. No. 5,252,458, which is incorporated herein by reference. An assay for the direct measurement of influenza neuraminidase was developed by Yolken et al. (J. Infectious Diseases 142 (1980) 516–523). Yolken et al. used the 4-methylumbelliferyl-2-ketoside of Neu5Ac as a fluorescent substrate to measure neuraminidase activity in preparations containing small quantities of cultivated virus as well as in some nasal wash specimens from human volunteers infected with the influenza virus. Yolken et al. suggested that "successful development of influenza neuraminidase might thus provide for a practical means of influenza diagnosis that is sufficiently rapid to allow for the institution of appropriate preventive and therapeutic interventions." According to Yolken et al., colorimetric assays were insufficiently sensitive for clinical applications, suggesting instead that fluorimetric assays for influenza neuraminidase might be suitable for detecting the virus in clinical samples.

Pachucki et al. (J. Clinical Microbiology 26 (1988) 2664–2666) tested the 4-methylumbelliferyl-2-ketoside of Neu5Ac on clinical specimens collected from influenza patients. Due to its low sensitivity, the assay was not useful in detecting neuraminidase in clinical specimens. The assay did, however, identify 91% of virus-positive isolates 25 hours after inoculation of tissue cultures.

The use of modified Neu5Ac substrates can increase the specificity of the neuraminidase assay. In sialic acids, the C4 position has been reported to play an important role in enzyme-substrate interactions. Further, since it is known that salivary bacterial enzymes exhibit neuraminidase activity (Varki et al., J. Biol. Chem. 258 (1983) 12465–12471), it is essential to avoid these undesired enzymatic activities. It has, for example, been shown that ketosides of 4-methoxy-Neu5Ac are resistant towards certain bacterial sialidases (Beau et al., Eur. J. Biochem. 106 (1980) 531–540).

U.S. Pat. No. 5,252,458 to Liav et al. provides a direct chromogenic assay for detecting a virus, including influenza viruses and parainfluenza viruses, that include in the virion a characteristic enzymatic activity, such as neuraminidase activity. The method, which is implemented in a clinic or physician's office, includes incubating a clinical sample suspected of containing the virus with a solution of a chromogenic substrate. The samples typically are obtained by swabbing the pharyngeal, or nasopharyngeal surfaces. If the virus is present, a chromogen is cleaved from the substrate, the chromogen is then reacted with a precipitating agent that intensifies the color, and the colored precipitate is concentrated for detection as a colored spot. The patent also discloses a kit for use in the clinic or physician's office that includes a filtration device for concentrating the colored precipitate into a spot.

U.S. Pat. No. 5,252,458 to Liav et al. provides synthetic routes for the synthesis of a precursor for chromogenic substrates that are useful in the diagnostic assay of viruses. Specifically the patent discloses syntheses for 4-alkoxy-N-acetylneuraminic acid.

U.S. Pat. No. 5,663,055 to Turner et al. discloses 4-modified Neu5Ac chromogenic substrates of viral neuraminidases for use in assays carried out in a clinic or a physician's office. The modification at position 4 includes hydrogen, fluorine, methoxy or ethoxy, and the substrate is sensitive to neuraminidases from influenza and parainfluenza viruses. Clinical samples are used in the assays, and distinct colors are produced as a result. The samples are typically pharyngeal, nasopharyngeal or respiratory secretions collected from patients as wash, swab, or expectorate specimens. U.S. Pat. No. 5,663,055 describes syntheses of several 4-modified derivatives of Neu5Ac, including 4-methoxy, 4-deoxy, and 4-fluoro derivatives. It further discloses syntheses for chromogenic ketosides of such 4-modified derivatives of Neu5Ac. This patent further establishes that 4-O-methyl chromogenic ketosides of Neu5Ac are selective for influenza virus A and for influenza virus B neuraminidases. These ketosides are insignificantly reactive with bacterial neuraminidases from the oral cavity, and are not significantly hydrolyzed by mammalian neuraminidase.

U.S. Pat. No. 5,719,020 to Liav et al. discloses 4,7-di-O-alkylated chromogenic ketosides of N-acetylneuraminic acid for use as the substrate in assays that are specific for influenza A and influenza B. The assays are performed in the clinic or physician's office. The chromophoric product may be precipitated and the colored precipitate concentrated for detection. Assays are also disclosed that permit discriminating between influenza A and influenza B on the one hand, and other viruses.

Although modification of the 4-position of Neu5Ac's provides specificity between certain viral and certain bacterial neuraminidase activities, it is still desirable to obtain substrates which provide enhanced specificity between the various viral neuraminidase reactivities while maintaining the specificity between viral and bacterial neuraminidase activities. Such substrates allow, for example, high specificity for particular types of neuraminidase-containing viruses and allow better and more directed treatment regimes. Use of specific substrates thus allows for more accurate surveillance of viral infections and more focused medical intervention as appropriate. U.S. Pat. No. 5,719,020, incorporated herein by reference, provides chromogenic and fluorogenic 4,7-disubstituted N-acetylneuraminic acid substrates for viral neuraminidase activities. These derivatives provide further specificity or differentiation between the various viral neuraminidase activities while maintaining the specificity between viral and bacterial neuraminidase activities. In particular, in U.S. Pat. No. 5,719,020 it is shown that the 4,7-modified Neu5Ac chromogenic substrates disclosed therein distinguish between influenza type A and B viruses on the one hand, and neuraminidases from other viral and bacterial pathogens on the other. A chromogenic derivative of 4-O-methyl Neu5Ac, however, develops color when exposed to parainfluenza virus types 1, 2, and 3, and mumps, in addition to influenza types A and B. Certain reactions leading to the synthesis of 4,7-di-O-alkyl Neu5Ac chromogenic ketosides disclosed in U.S. Pat. No. 5,719,020 likewise are inefficient and provide poor purity and low yields.

The synthetic procedures leading to various 4-O-alkyl Neu5Ac derivatives are disclosed in U.S. Pat. No. 5,556,963, but have certain difficulties associated with them. These include the provision of synthetic routes involving a large number of distinct chemical reactions. These require an excessive number of unit operations, leading to the need for many reagents, solvents, pieces of laboratory apparatus, and for extended time to obtain the product. Additionally, with respect to the objectives of the present invention, the syntheses in U.S. Pat. No. 5,556,963 do not provide the 4-O-alkyl Neu5Ac chromogenic ketosides that serve as substrates for viral neuraminidases. The syntheses of 4-O-alkyl Neu5Ac chromogenic ketosides described in U. S. Pat. No. 5,663,055 are generally cumbersome and inefficient, involving, for example, the need to transfer the reactant between aqueous and organic phases using a phase transfer reagent.

Zbiral et al. (Liebigs Ann. Chem 1989:519–526) studied the 4-methylumbelliferyl α ketosides of 7-epi Neu5Ac, 7,8-(bis)epi Neu5Ac, 7-deoxy Neu5Ac and 4,7-dideoxy Neu5Ac, among others, as substrates for neuraminidase from *Vibrio cholerae*. It was shown that the glycosidic hydrolysis was significantly slowed only for 7,8-(bis)epi Neu5Ac, 7-deoxy Neu5Ac and 4,7-dideoxy Neu5Ac of those derivatives tested. Zbiral et al. (Monatshefte Chem. 119:127–141 (1988)) synthesized 7-, 8-, and 9-, monodeoxy derivatives of Neu5Ac and 4,7-dideoxy Neu5Ac with the objective of studying their activation by cytidine monophosphate-sialate synthase. U.S. Pat. No. 5,719,020 reports that 5-bromo-3-indolyl 4,7-di-O-methyl Neu5Ac ketoside is selectively hydrolyzed by the neuraminidase activity of only influenza types A and B, whereas 5-bromo-3-indolyl 4-O-methyl Neu5Ac ketoside is acted upon by influenza types A and B, as well as by the neuraminidase activity of parainfluenza types 1 and 2, and mumps, but not significantly by the enzyme of parainfluenza type 3, and not at all by respiratory syncytial adenovirus. Thus there is important selectivity manifested at the 4- and 7-positions of Neu5Ac which suggests that 7-O-alkyl Neu5Ac chromogenic ketosides afford the potential of considerable selectivity among bacterial and viral neuraminidases.

The present invention addresses the deficiencies identified above related to the preparation of 4-alkyl chromogenic glycosides and 7-alkyl chromogenic glycosides of N-acetylneuraminic acids. As set forth in detail herein, the number of synthetic steps and attendant number of unit operations is reduced. The use of chromatographic separations likewise is reduced to the extent possible. Additionally, the synthetic reactions have been optimized and the recovery procedures enhanced to provide high step yields and thereby high overall yields for the final products that are unexpected by the present state of knowledge in the field. The resulting improvements permit economical preparation of viral neuraminidase substrates on the scale of kilograms for commercial sale.

SUMMARY OF THE INVENTION

The present invention discloses a method of preparing a 4-O-alkyl chromogenic ketoside of N-acetylneuraminic acid (Neu5Ac)that includes the steps of:

(a) alkylating Neu5Ac on its C1 carboxyl and anomeric C2 hydroxyl to provide an alkyl ester alkyl ketoside derivative of Neu5Ac;

(b) protecting the 8- and 9-hydroxyl groups of the alkyl ester alkyl ketoside derivative of Neu5Ac to form a protected alkyl ester alkyl ketoside derivative of Neu5Ac;

(c) alkylating the 4-hydroxyl group of the protected alkyl ester alkyl ketoside derivative of Neu5Ac by contacting it with a composition containing an alkyl halide to form a 4-O-alkyl protected alkyl ester alkyl ketoside derivative of Neu5Ac;

(d) selectively deprotecting the 8- and 9-hydroxyl groups and dealkylating the 2-hydroxyl group of the ketoside derivative obtained in step (c), and derivatizing the resulting 2-, 7-, 8-, and 9-hydroxyl groups;

(e) activating the anomeric carbon of the product obtained in step (d) to form a 4-O-alkyl alkyl ester derivative of Neu5Ac, derivatized at the 7-, 8- and 9-hydroxyls, and activated at the anomeric carbon;

(f) contacting the product obtained in step (e) with a suspension of a chromogenic moiety in a solvent to form a chromogenic ketoside of a 4-O-alkyl alkyl ester derivative of Neu5Ac, derivatized at the 7-, 8- and 9-hydroxyls; and (g) obtaining a 4-O-alkyl chromogenic ketoside of Neu5Ac from the derivatized chromogenic ketoside obtained in step (f).

In important embodiments of the method, protecting the 8- and 9-hydroxyl groups described in step (b) involves forming a ketal or an 8,9-epoxide. In additional important embodiments, the alkyl halide employed in step (c) is methyl iodide and the composition further comprises either silver oxide or a mixture of barium oxide and barium hydroxide.

In significant embodiments of the method, the activation of the anomeric carbon described in step (e) involves placing a halo substituent, such as chloro, on the anomeric carbon.

In further advantageous embodiments, the chromogenic moiety described in step (f) is chosen from a wide variety of chromogenic, luminescent, or chemiluminescent moieties, and in a more advantageous embodiment, the chromogenic moiety is 5-bromo-3-indolyl.

In additional significant embodiments of the method, alkyl groups on the C1 carboxyl, the anomeric hydroxyl, and the 4-position are the same or different and are chosen from the group consisting of methyl, ethyl, propyl, isopropyl, and normal or branched butyl; more significantly, they are all methyl groups.

In a preferred embodiment, a method of preparing a 4-O-methyl chromogenic ketoside of N-acetylneuraminic acid (Neu5Ac) is presented, including the following sequential steps:

(a) contacting Neu5Ac with methanol and the protonated form of a cation exchange resin to methylate the C1 carboxyl group and the C2 hydroxyl group, forming a methyl ester methyl ketoside of Neu5Ac;

(b) contacting the methylated ester ketoside of Neu5Ac provided in step (a) with acetone and p-toluenesulfonic acid, to form a 8,9-isopropylidene methyl ester methyl ketoside of Neu5Ac;

(c) contacting the 8,9-isopropylidene methylated ester ketoside of Neu5Ac provided in step (b) with methyl iodide and silver oxide to form a 4-O-methyl 8,9-isopropylidene methylated ester ketoside of Neu5Ac;

(d) selectively removing the 8,9-isopropylidene and C2 methyl groups from the ketoside product obtained in step (c) and acetylating the anomeric, 7-, 8- and 9-hydroxyl groups of the resulting intermediate;

(e) activating the anomeric carbon of the product obtained in step (d) by converting the acetate to chloride;

(f) contacting the activated chloride product provided in step (e) with a suspension of a derivative of 5-bromo-3-indolol and potassium tert-butoxide in a solvent to form a chromogenic ketoside of a 4-O-methyl methyl ester of Neu5Ac, acetylated at the 7-, 8- and 9-hydroxyls; and (g) deblocking the acetyl groups at the 8- and 9-hydroxyl groups and the methyl ester from the chromogenic ketoside of Neu5Ac obtained in step (f), to form the 4-O-methyl chromogenic ketoside of Neu5Ac.

In another preferred embodiment, a method of preparing a 4-O-methyl chromogenic ketoside of N-acetylneuraminic acid (Neu5Ac) includes the following sequential steps:

(a) contacting Neu5Ac with methanol and the protonated form of a cation exchange resin to methylate the C1 carboxyl group and the C2 hydroxyl group, forming a methyl ester methyl ketoside of Neu5Ac;

(b) contacting the methylated ester ketoside of Neu5Ac provided in step (a) with
 (i) an acid chloride of an organic sulfonic acid, and
 (ii) treating the result obtained in step (b) (i) with a composition containing sodium methoxide and methanol, providing an 8,9-epoxide methyl ester methyl ketoside of Neu5Ac;

(c) methylating the 4-hydroxyl group of the 8,9-epoxide methylated ester ketoside of Neu5Ac provided in step (b) by a process chosen from the group consisting of
 (i) contacting the epoxide ketoside with a composition containing methyl iodide and silver oxide,
 (ii) contacting the epoxide ketoside with a composition containing dimethylsulfate and sodium hydride, and
 (iii) a sequential combination of step (c)(i) and step (c)(ii), providing a 4-O-methyl 8,9-epoxide methylated ester ketoside of Neu5Ac;

(d) selectively removing the 8,9-epoxide and C2 methyl groups of the ketoside product obtained in step (c) and acetylating the anomeric, 7-, 8- and 9-hydroxyl groups of the resulting intermediate;

(e) activating the anomeric carbon of the product obtained in step (d) by converting the acetate to chloride;

(f) contacting the activated chloride product provided in step (e) with a suspension of a derivative of 5-bromo-3-indolol and potassium tert-butoxide in a solvent to form a chromogenic ketoside of a 4-O-methyl methyl ester of Neu5Ac, acetylated at the 7-, 8- and 9-hydroxyls; and (g) deblocking the acetyl groups at the 8- and 9-hydroxyl groups and the methyl ester from the chromogenic ketoside of Neu5Ac obtained in step (f), to form the 4-O-methyl chromogenic ketoside of Neu5Ac.

The present invention further provides a method of preparing a 7-O-alkyl chromogenic ketoside of N-acetylneuraminic acid (Neu5Ac) that includes the following steps in order:

(a) alkylating Neu5Ac on the C1 carboxyl and C2 (anomeric) hydroxyl to provide an alkyl ester alkyl ketoside derivative of Neu5Ac;

(b) protecting the 8- and 9-hydroxyl groups of the alkyl ester alkyl ketoside derivative of Neu5Ac to form a protected alkyl ester alkyl ketoside derivative of Neu5Ac;

(c) blocking the 4-hydroxyl group of the protected alkyl ester alkyl ketoside derivative of Neu5Ac with a blocking group to form a blocked protected alkyl ester alkyl ketoside derivative of Neu5Ac;

(d) alkylating the 7-hydroxyl group of the blocked protected alkyl ester alkyl ketoside derivative of Neu5Ac by contacting the derivative with a composition comprising an alkyl halide to form a 7-O-alkyl blocked protected alkyl ester alkyl ketoside derivative of Neu5Ac;

(e) deblocking the 7-O-alkyl blocked protected alkyl ester alkyl ketoside derivative of Neu5Ac to form a 7-O-alkyl protected alkyl ester alkyl ketoside derivative of Neu5Ac;

(f) selectively deprotecting the 8- and 9-hydroxyl groups and dealkylating the 2-hydroxyl group of the ketoside product obtained in step (e), and derivatizing the 2-, 4-, 8-, and 9-hydroxyl groups of the resulting product;

(g) activating the anomeric carbon of the product obtained in step (f) to form a 7-O-alkyl alkyl ester derivative of Neu5Ac, derivatized at the 4-, 8- and 9-hydroxyls, and activated at the anomeric carbon;

(h) contacting the product obtained in step (g) with a suspension of a chromogenic moiety in a solvent to form a chromogenic ketoside of a 7-O-alkyl alkyl ester derivative of Neu5Ac, derivatized at the 4-, 8- and 9-hydroxyls; and (i) obtaining a 7-O-alkyl chromogenic ketoside of Neu5Ac from the derivatized chromogenic ketoside obtained in step (h).

In advantageous embodiments of the method, protecting the 8- and 9-hydroxyl groups described in step (b) includes forming a ketal or an 8,9-epoxide. Additionally, in an important embodiment, the blocking group in step (c) is benzyl.

In a significant embodiment, the activation of the anomeric carbon described in step (g) includes placing a halo substituent, preferably a chloro, on the anomeric carbon. In further significant embodiments, a wide variety of chromogenic moieties may be employed in step (h); preferably the chromogenic moiety is 5-bromo-3-indolyl.

In further important embodiments, the alkyl group on the C1 carboxyl, the alkyl group on the anomeric hydroxyl, and the alkyl group at the 7-position are the same or different and are chosen from among methyl, ethyl, propyl, isopropyl, and normal or branched butyl; preferably all three groups are methyl.

The invention further provides a method of preparing a 7-O-methyl chromogenic ketoside of N-acetylneuraminic acid (Neu5Ac) that includes the following sequential steps:

(a) contacting Neu5Ac with methanol and the protonated form of a cation exchange resin to methylate the C1 carboxyl group and the C2 hydroxyl group, forming a methyl ester methyl ketoside of Neu5Ac;

(b) contacting the methylated ester ketoside of Neu5Ac provided in step (a) with acetone and p-toluenesulfonic acid, to form an 8,9-isopropylidene methyl ester methyl ketoside of Neu5Ac;

(c) blocking the 4-hydroxyl group of the 8,9-isopropylidene methyl ester methyl ketoside of Neu5Ac with a blocking group to form a blocked 8,9-isopropylidene methyl ester methyl ketoside of Neu5Ac;

(d) contacting the blocked 8,9-isopropylidene methyl ester methyl ketoside of Neu5Ac provided in step (c) with methyl iodide and a mixture of barium oxide and barium hydroxide to form a 7-O-methyl blocked 8,9-isopropylidene methyl ester methyl ketoside of Neu5Ac;

(e) deblocking the 7-O-methyl blocked 8,9-isopropylidene methyl ester methyl ketoside of Neu5Ac to form a 7-O-methyl 8,9-isopropylidene methyl ester methyl ketoside of Neu5Ac;

(f) selectively removing the 8,9-isopropylidene and C2 methyl groups from the ketoside product obtained in step (e) and acetylating the anomeric, 7-, 8- and 9-hydroxyl groups of the resulting intermediate;

(g) activating the anomeric carbon of the product obtained in step (f) by converting the acetate to chloride;

(h) contacting the activated chloride product provided in step (g) with a suspension of a derivative of 5-bromo-3-indolol and potassium tert-butoxide in a solvent to form a chromogenic ketoside of a 7-O-methyl methyl ester of Neu5Ac, acetylated at the 7-, 8- and 9-hydroxyls; and (i) deblocking the acetyl groups at the 7-, 8- and 9-hydroxyl groups and the methyl ester from the chromogenic ketoside of Neu5Ac obtained in step (h), to form the 7-O-methyl chromogenic ketoside of Neu5Ac.

Additionally the invention discloses a method of preparing a 7-O-methyl chromogenic ketoside of N-acetylneuraminic acid (Neu5Ac) that includes, in order, the following steps:

(a) contacting Neu5Ac with methanol and the protonated form of a cation exchange resin to methylate the C1 carboxyl group and the C2 hydroxyl group, forming a methyl ester methyl ketoside of Neu5Ac;

(b) contacting the methylated ester ketoside of Neu5Ac provided in step (a) with
 (i) an acid chloride of an organic sulfonic acid, and
 (ii) treating the result obtained in step (b) (i) with a composition containing sodium methoxide and methanol, providing an 8,9-epoxide methyl ester methyl ketoside of Neu5Ac;

(c) blocking the 4-hydroxyl group of the 8,9-epoxide methyl ester methyl ketoside of Neu5Ac with a blocking group to form a blocked 8,9-epoxide methyl ester methyl ketoside of Neu5Ac;

(d) methylating the 7-hydroxyl group of the blocked 8,9-epoxide methylated ester ketoside of Neu5Ac provided in step (c) by a process chosen from the group consisting of
 (i) contacting the epoxide ketoside with a composition containing methyl iodide and silver oxide,
 (ii) contacting the epoxide ketoside with a composition containing dimethylsulfate and sodium hydride, and
 (iii) a sequential combination of step (c)(i) and step (c)(ii), providing a 7-O-methyl blocked 8,9-epoxide methylated ester ketoside of Neu5Ac;

(e) deblocking the 7-O-blocked methyl blocked 8,9-epoxide methyl ester methyl ketoside of Neu5Ac to form a 7-O-methyl 8,9-isopropylidene methyl ester methyl ketoside of Neu5Ac;

(f) selectively removing the 8,9-epoxide and C2 methyl groups of the ketoside product obtained in step (e) and acetylating the anomeric, 4-, 8- and 9-hydroxyl groups of the resulting intermediate;

(g) activating the anomeric carbon of the product obtained in step (f) by converting the acetate to chloride;

(h) contacting the activated chloride product provided in step (g) with a suspension of a derivative of 5-bromo-3-indolol and potassium tert-butoxide in a solvent to form a chromogenic ketoside of a 7-O-methyl methyl ester of Neu5Ac, acetylated at the 4-, 8- and 9-hydroxyls; and (i) deblocking the acetyl groups at the 4-, 8- and 9-hydroxyl groups and the methyl ester from the chromogenic ketoside of Neu5Ac obtained in step (h), to form the 7-O-methyl chromogenic ketoside of Neu5Ac.

DESCRIPTION OF PREFERRED EMBODIMENTS

This invention describes improved synthetic processes for the preparation of 4-alkylated and 7-alkylated chromogenic derivatives of Neu5Ac in quantities suitable for commercial development. In general, the chromogenic substrates, which contain the chromogenic moiety in ketosidic linkage with the Neu5Ac derivative, interact poorly with light so that they neither absorb nor emit light to a significant extent. However, when acted upon by the viral neuraminidase, the chromogenic substrate liberates the chromogenic moiety as a free compound, no longer bound in ketosidic linkage to the derivatized Neu5Ac. The free chromogenic moiety in its most general sense, interacts with light to a significant extent either absorbing light at a particular wavelength (serving as a chromophore) or emitting light of a particular wavelength from an excited state. The excited state may arise from exposure to appropriate exciting radiation, or from chemically-induced excitation. These give rise respectively to luminescence, which comprises fluorescence and phosphorescence, and chemiluminescence. As used herein and for purposes of providing a convenient shorthand reference, the term "chromogenic" describes moieties that may be detectable by any of these processes, namely, absorption of light of a characteristic wavelength, and emission of light at a characteristic wavelength by fluorescence, phosphorescence, or chemiluminescence.

The substrates that are synthesized by the processes disclosed in this invention are characterized generally by the formula wherein $R_1$=H or X, and $R_2$=H or X, but only one of $R_1$ or $R_2$ may be X in any given substrate; and wherein X is chosen from among methyl, ethyl, propyl, isopropyl, and normal or branched butyl. The 2-ketoside is linked to the chromogenic moiety Y in the α anomeric configuration. In general Y may be any chromogenic moiety such that, when cleaved by the action of a neuraminidase, the alcohol HOY is chromogenic within the meaning of this disclosure. Examples of chromophoric and fluorescent chromogenic moieties designated by Y include 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl. Additionally, Y may generally be a radical such that the hydrolysis product HOY exhibits phosphorescence or chemiluminescence.

Accordingly, the corresponding chromogenic substrates synthesized in this invention include 4-methylumbelliferyl 4-O-alkyl Neu5Ac ketoside, 3-cyanoumbelliferyl 4-O-alkyl Neu5Ac ketoside, 2-nitrophenyl 4-O-alkyl Neu5Ac ketoside, 4-nitrophenyl 4-O-alkyl Neu5Ac ketoside, 3-resorufin 4-O-alkyl Neu5Ac ketoside, 5-bromo-4-chloro-3-indolyl 4-O-alkyl Neu5Ac ketoside, 5-bromo-3-indolyl 4-O-alkyl Neu5Ac ketoside, 3-indolyl 4-O-alkyl Neu5Ac ketoside, nitrophenylazophenyl 4-O-alkyl Neu5Ac ketoside, nitrophenylazoresorcinyl 4-O-alkyl Neu5Ac ketoside, 3-methoxyphenyl 4-O-alkyl Neu5Ac ketoside, 3-dimethylaminophenyl 4-O-alkyl Neu5Ac ketoside, 4-chloro-1-naphthyl 4-O-alkyl Neu5Ac ketoside, and 6-bromo-2-naphthyl 4-O-alkyl Neu5Ac ketoside; and in addition a luminescent 4-O-alkyl Neu5Ac ketoside and a chemiluminescent 4-O-alkyl Neu5Ac ketoside.

Additionally, the chromogenic substrates include 4-methylumbelliferyl 7-O-alkyl Neu5Ac ketoside, 3-cyanoumbelliferyl 7-O-alkyl Neu5Ac ketoside, 2-nitrophenyl 7-O-alkyl Neu5Ac ketoside, 4-nitrophenyl 7-O-alkyl Neu5Ac ketoside, 3-resorufin 7-O-alkyl Neu5Ac ketoside, 5-bromo-4-chloro-3-indolyl 7-O-alkyl Neu5Ac ketoside, 5-bromo-3-indolyl 7-O-alkyl Neu5Ac ketoside, 3-indolyl 7-O-alkyl Neu5Ac ketoside, nitrophenylazophenyl 7-O-alkyl Neu5Ac ketoside, nitrophenylazoresorcinyl 7-O-alkyl Neu5Ac ketoside, 3-methoxyphenyl 7-O-alkyl Neu5Ac ketoside, 3-dimethylaminophenyl 7-O-alkyl Neu5Ac ketoside, 4-chloro-1-naphthyl 7-O-alkyl Neu5Ac ketoside, and 6-bromo-2-naphthyl 7-O-alkyl Neu5Ac ketoside; and in addition a luminescent 7-O-alkyl Neu5Ac ketoside and a chemiluminescent 7-O-alkyl Neu5Ac ketoside.

Figure 1:
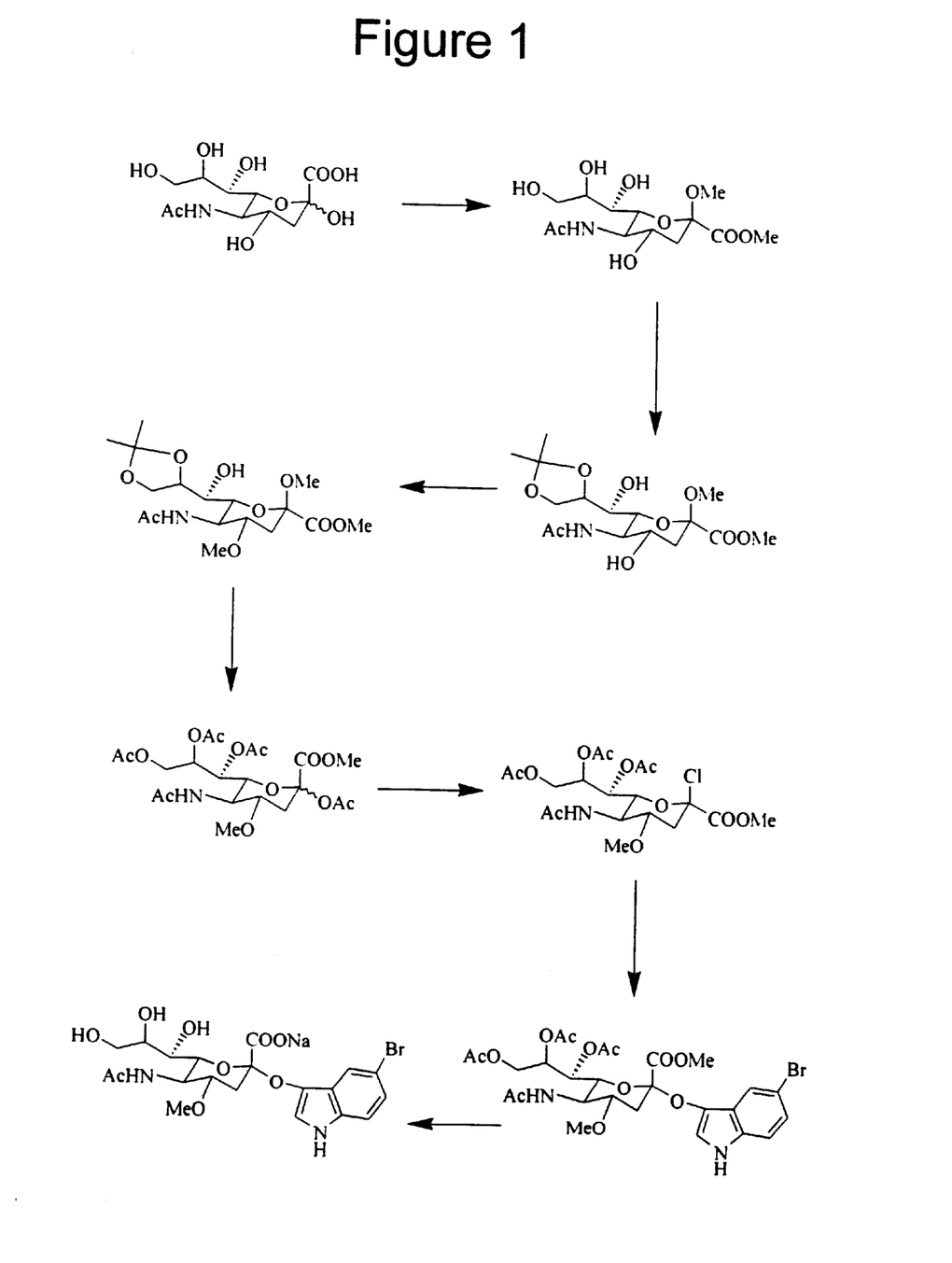
FIG. 1. Reaction flow diagram providing 5-bromo-3-indolyl 4-O-methyl Neu5Ac ketoside from Neu5Ac.
Figure 2:
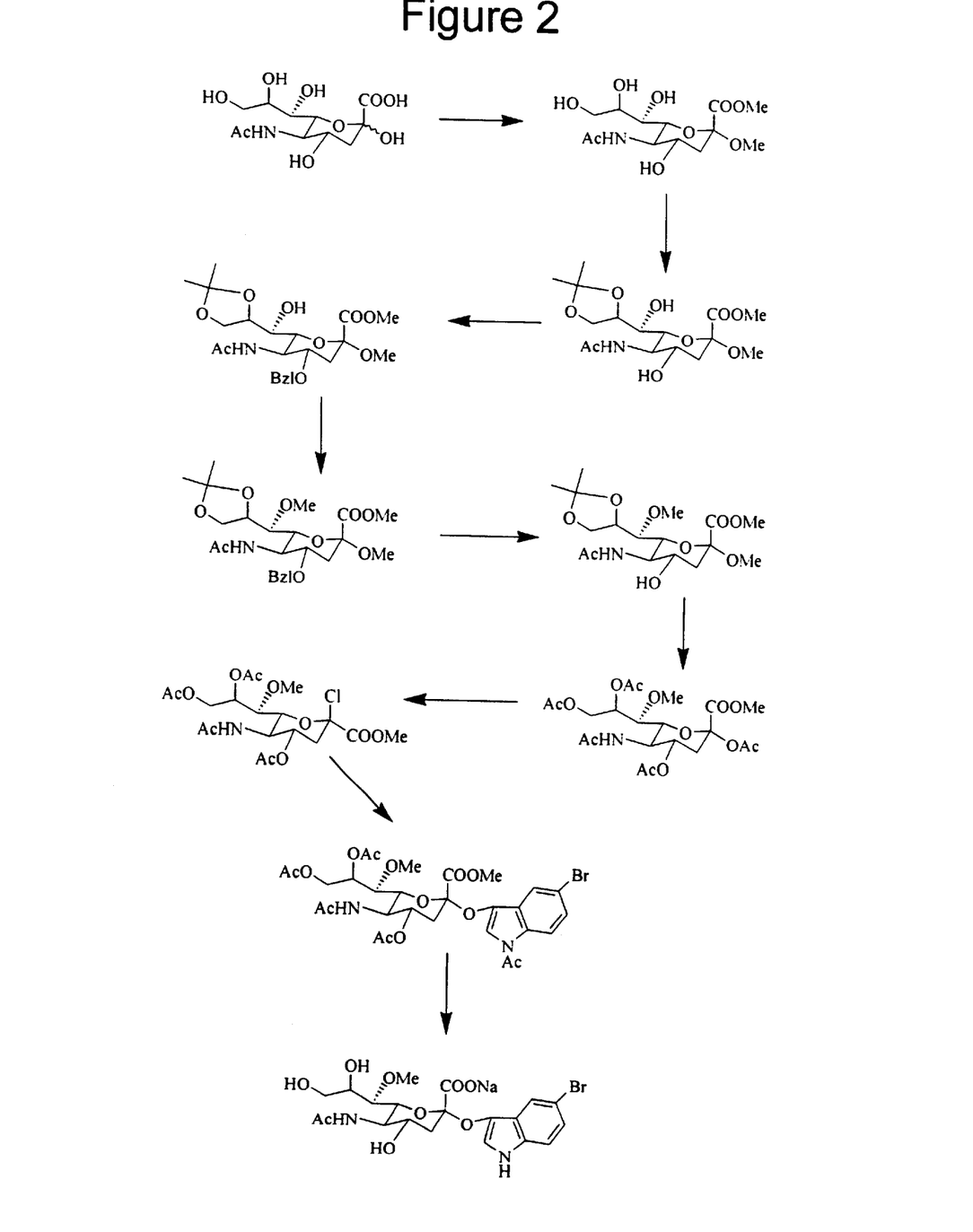
FIG. 2. Reaction flow diagram providing 5-bromo-3-indolyl 7-O-methyl Neu5Ac ketoside from Neu5Ac.

The syntheses disclosed herein improve on reactions and processes set forth in U.S. Pat. No. 5,556,963 (relating to 4-O-alkyl Neu5Ac), U.S. Pat. No. 5,663,055 (relating to 4-O-alkyl Neu5Ac chromogenic ketosides) and U.S. Pat. No. 5,719,020 (relating to 4,7-di-O-alkyl Neu5Ac chromogenic ketosides), whose disclosures are hereby incorporated by reference. The description of this invention is provided below in general terms, however, in preferred embodiments the alkyl groups employed at intermediate stages in the syntheses, and the alkyl groups incorporated at the 4-position or the 7-position in the final products, are methyl. Reaction flow diagrams providing 5-bromo-3-indolyl 4-O-methyl Neu5Ac ketoside, and 5-bromo-3-indolyl 7-O-methyl Neu5Ac ketoside, from Neu5Ac, are shown respectively in FIG. 1 and FIG. 2.

The starting material is Neu5Ac, which is available from MediHerb Inc. (4540 S. Navajo #1, Englewood Colo. 80110). Neu 5Ac is first converted to a dimethyl derivative wherein the carboxyl of C1 and the anomeric hydroxyl on C2 are methylated simultaneously in a single reaction. Typically this can be effected by treatment with methanol under conditions of acid catalysis. A useful and effective acid catalyst is the protonated form of a strong acid cation exchange resin, such as Bio-Rad protonated resin Nafion™ (Hercules, Calif.). The result is a methyl ester methyl ketoside of Neu5Ac [2]:

[2]

Crude yields range from about 90% to about 96%, providing a yield upon crystallization of about 65% for this step. Other well known cation exchange resins were tried but provided poor yields for this step. Furthermore, soluble strong acids such as HCl, sulfuric acid, trifluoroacetic acid and a sulfonic acid provided a product in which only the ester group was formed. Thus the use of a protonated cation exchange resin led to an important reduction in the number of reactions required for these syntheses, without sacrificing step yield.

In the next step the 8,9-vicinal diol group is protected by a specific reaction. In a preferred embodiment this protection is afforded by preparation of an 8,9-isopropylidene derivative, the ketal provided by reaction with acetone under acid catalysis. Useful acid catalysts include p-toluenesulfonic acid, salts of p-toluenesulfonic acid such as pyridinium p-toluenesulfonate, and acidic salts such as $ZnCl_2$ and $FeCl_3$. A preferred acid catalyst for ketal formation is p-toluenesulfonic acid. Use of this catalyst affords protection of the 8,9 dihydroxy grouping in a single step, providing the ketal in essentially quantitative yield requiring no chromatography for purification. The result is an 8,9-isopropylidene Neu5Ac methyl ester methyl ketoside [3]:

[3]

In an alternative embodiment, the protective grouping for the 8,9-diol involves formation of an epoxide. This is a two-step reaction in which first an aryl- or alkyl-sulfonyl chloride derivatives the 9-hydroxyl group. This intermediate is then induced to cyclize by the addition of sodium methoxide, yielding an 8,9-epoxide derivative of the Neu5Ac methyl ester methyl ketoside [4]:

[4]

Preferred acid chlorides include methanesulfonyl chloride, p-toluenesulfonyl chloride, and 2-mesitylenesulfonyl chloride. In this procedure, purification by silica gel chromatography is employed, providing a step yield of about 65%.

The next stage in the syntheses generates either the 4-alkylated derivative of the protected and methylated Neu5Ac, or the 7-alkylated derivative thereof. In general the alkyl groups at the 4-position or the 7-position may be methyl, ethyl, propyl, isopropyl, and normal or branched butyl. In preferred embodiments of the invention, the synthetic reactions employed at this stage of the method provide the 4-O-methyl derivative or the 7-O-methyl derivative. U.S. Pat. No. 5,719,020 discloses that, generally a mixture of the 4-monoalkylated derivative and the 4,7-dialkylated derivative is obtained by the methods disclosed therein. It appears from discussion in the patent that the 7-hydroxyl is in a more sterically hindered environment than the 4-hydroxyl when the 8,9-dihydroxy grouping is protected by the isopropylidene substituent, and thereby is more difficult to alkylate successfully.

The procedures disclosed in the present invention reflect this apparent distinction in reactivity. In order to alkylate the 4-hydroxyl group, a straightforward alkylation, using reactions described in the following, suffice, with minimal side reaction at the 7-hydroxyl group. In contrast, in order to prepare the 7-alkyl derivative, it is advantageous first to block the 4-hydroxyl with a suitable blocking group. Any blocking procedure may be used so long as it is selective for the 4-hydroxyl while leaving the 7-hydroxyl free for alkylation. Once so protected, the 7-hydroxyl is readily alkylated, and then the blocking group is immediately removed.

The actual reaction procedures used for preparing the 4-O-alkylated derivative or the 7-O-alkylated derivative are affected by choice of the 8,9-protecting group used in the previous reaction step, that is, the isopropylidene group or the epoxide group, as well as by the intended site of alkylation, that is, the 4-hydroxyl or the 7-hydroxyl. As contemplated herein, alkylation may generally be achieved by reaction with an alkyl halide, preferably a higher halide such as bromide or iodide, in the presence of a basic substance. As noted above, the alkyl group may be methyl, ethyl, propyl, isopropyl, and normal or branched butyl. In a preferred embodiment of the method of the invention, the reagent employed in this reaction is methyl iodide, leading to the synthesis of the 4-O-methyl derivative or the 7-O-methyl derivative. In general the base may be a solid heavy metal oxide or hydroxide. In preferred embodiments, the base employed may be silver oxide, or it may be a mixture of barium oxide with barium hydroxide octahydrate.

In a preferred embodiment of the method employing the isopropylidene grouping to provide the 4-O-methyl methyl ester methyl ketoside [5] ($R_1$=Me and $R_2$=H), the reaction is carried out using methyl iodide in the presence of silver oxide. This reaction provides a yield, after crystallization, of about 80%.

[5]

In a preferred embodiment of the reaction path used to synthesize the 7-methyl derivative based on the use of the isopropylidene grouping, the 4-hydroxyl group was first blocked by reaction with benzyl bromide under basic conditions. This reaction proceeds with some difficulty; it was found that when the base employed is silver oxide only a modest yield (12%) was obtained. Upon experimentation, it was found that if sodium hydride is employed as a base, the yield of the 4-O-benzyl 8,9-isopropylidene Neu5Ac methyl ester methyl ketoside [5] ($R_1$=Bzl and $R_2$=H) increases to 32%. Since the poor yield obtained with silver oxide posed a problem, and since the yield surprisingly improved by almost a factor of 3 when sodium hydride was used instead, it is clear that the latter conditions provide unexpectedly advantageous results. The 4-O-benzyl 8,9-isopropylidene Neu5Ac methyl ester methyl ketoside is then methylated at the 7 position using methyl iodide in the presence of barium oxide with barium hydroxide octahydrate to provide the protected product [5] ($R_1$=Bzl and $R_2$=Me).

Once methylated at the 7-position, the product is deprotected by catalytic hydrogenation. The last two steps proceed almost quantitatively and provides the 7-O-benzyl 8,9-isopropylidene Neu5Ac methyl ester methyl ketoside [5] ($R_1$=H and $R_2$=Me); thus the overall yield for the protection-methylation-deprotection sequence is on the order of 30%, being limited in this embodiment at the step of placing the benzyl blocking group on the 4-hydroxyl.

The reaction strategies yielding the 4-methyl 8,9-protected Neu5Ac methyl ester methyl ketosides and 7-methyl 8,9-protected Neu5Ac methyl ester methyl ketosides described above represent a significant and unexpected improvement over the results predicted from the state of the art available at the time this invention was made. As noted in U.S. Pat. No. 5,719,020, excess alkylating agent, such as dimethylsulfate, when employed to treat the 8,9-ketal protected Neu5Ac methyl ester methyl ketoside, yields a mixture of the 4-monoalkyl and the 4,7-dialkyl derivatives. Additionally, synthesis of the 7-alkyl derivatives appears unknown at all in the art at the time this invention was made.

From this point on, the synthetic steps involving the 4-methyl derivative and the 7-methyl derivative, leading to the respective chromogenic ketosides, are generally comparable or closely similar. The 8,9-protected mono-O-alkyl Neu5Ac methyl ester methyl ketosides are next deesterified, deprotected at the 8,9 position, and demethylated at the anomeric position. Then the deprotected and demethylated 4-methyl or 7-methyl Neu5Ac is reesterified, and derivatized at the remaining hydroxyl groups, including the anomeric hydroxyl, by acetylation. A series of steps is undertaken in which purification of intermediates need not be carried out, and only the product of the last step, namely, the tetraacetylated derivative [6], is purified. The product at this stage is the same whether the starting substance is protected by the isopropylidene group or by the epoxide group at the 8- and 9-positions. Specifically, in the preferred embodiment outlined herein, the product obtained in this set of reactions is either a 2,7,8,9-tetraacetyl derivative of 4-O-methyl Neu5Ac methyl ester ([6], $R_1$=Me and $R_2$=Ac) or a 2,4,8,9-tetraacetyl derivative of 7-O-methyl Neu5Ac methyl ester ([6], $R_1$=Ac and $R_2$=Me; these intermediates, and those in the following description that are maximally derivatized with acetyl groups, are referred to as the peracetylated derivatives herein):

The deesterification of the 4-alkyl derivative or the 7-alkyl derivative is carried out under alkaline conditions in aqueous alcohol. Beneficially the alcohol used corresponds to the alkyl group present at the 4- and 7-positions. After neutralization of the aqueous alkali, the isopropylidine and anomeric methyl groups are hydrolyzed under acidic conditions; in a preferred embodiment this step employs a protonated cation exchange resin (e.g., Bio-Rad™ ($H^+$) resin) in the presence of dilute aqueous acid. The deprotected derivative is then dried and contacted with anhydrous alcohol in the presence of a strong anhydrous acid. After drying again, the peracetylated derivatives of the monoalkyl Neu5Ac methyl esters are obtained by acetylation using acetic anhydride in pyridine, in the presence of an organic base such as dimethylaminopyridine. In the case where the 4- and 7-alkyl substituents are methyl, yields of the peracetylated products are about 70–75% based on the monomethyl 8,9-protected Neu5Ac methyl ester methyl ketosides.

The subsequent step activates the anomeric position by specifically displacing the anomeric acetate group with chloride. Thus a peracetylated derivative of 4-O-alkyl Neu5Ac methyl ester or 7-O-alkyl Neu5Ac methyl ester is converted into a 2-chloro-triacetyl derivative of 4-O-alkyl Neu5Ac methyl ester or 7-O-alkyl Neu5Ac methyl ester. As noted, these are activated derivatives that can readily be used to generate the desired chromogenic glycoside. The activation is readily accomplished by treating the peracetylated derivative with anhydrous HCl in the presence of acetyl chloride. Alternatively, the reaction may be carried out by treating the derivative with anhydrous HCL in dichloromethane. In general, the step yields for these reactions are high. The structures of the 4-O-methyl derivative [7] ($R_1$=Me and $R_2$=Ac) or the 7-O-methyl derivative [7] ($R_1$=Ac and $R_2$=Me) are as shown:

Chromogenic ketosides of the peracetylated derivatives of the 4-alkyl Neu5Ac methyl ester or the 7-alkyl Neu5Ac methyl ester are prepared by contacting a product of the preceding reaction, that is, the corresponding 2-chloro-triacetylated derivative such as [7], with a composition that generates a reactive form of the chromogenic moiety. In an advantageous embodiment, the reactive form includes the oxyanion derivative of the chromogenic moiety. This reactive form may then displace the 2-chloro group of the 2-chloro-peracetylated derivative of 4-alkyl Neu5Ac methyl ester or the 7-alkyl Neu5Ac methyl ester, yielding a peracetylated derivative of the 4-alkyl Neu5Ac methyl ester chromogenic ketoside or the 2-chloro-peracetylated derivative of the 7-alkyl Neu5Ac methyl ester chromogenic ketoside. In the preferred embodiments set forth above, the peracetylated 4-O-methyl chromogenic ketoside ($R_1$=Me and $R_2$=Ac) or of the peracetylated 7-O-methyl chromogenic ketoside ($R_1$=Ac and $R_2$=Me), in which the chromogenic moiety is the 5-bromo-3-indolyl group, have the structure [8]:

The reaction proceeds advantageously in a variety of implementations. In one implementation, the chromogenic moiety derivatized with acetate is brought into contact with a 2-chloro-triacetylated derivative of the 4-alkyl Neu5Ac methyl ester or of the 7-alkyl Neu5Ac methyl ester, in the presence of strong base such as an alkali metal alkoxide in an aprotic solvent. The product obtained may subsequently be reacetylated using acetic anhydride in pyridine in a fashion similar to the acetylation described above. In another embodiment of this step, the chromogen acetate is suspended in acetone solution and aqueous sodium hydroxide is added. A 2-chloro-triacetylated derivative of 4-alkyl Neu5Ac methyl ester or the 7-alkyl Neu5Ac methyl ester is slowly added and alkaline conditions are maintained. In yet another implementation of this step, the chromogen acetate is suspended in an aprotic organic solvent and solid potassium hydroxide is added. A 2-chloro-triacetylated derivative of 4-alkyl Neu5Ac methyl ester or the 7-alkyl Neu5Ac methyl ester is then added. In general, a peracetylated derivative of the 4-alkyl Neu5Ac methyl ester chromogenic ketoside or the 7-alkyl Neu5Ac methyl ester chromogenic ketoside is purified in these implementations by silica gel chromatography. When the 4- or the 7-alkyl group is methyl, step yields range from about 60% to about 75%.

The peracetylated derivative of a 4-alkyl Neu5Ac methyl ester chromogenic ketoside or the 7-alkyl Neu5Ac methyl ester chromogenic ketoside is deprotected in a single procedure by the base catalyzed cleavage of the various ester groups. For example, the ketoside may be treated first with sodium methoxide in methanol, and then, without purification, by the addition of aqueous sodium hydroxide. The desired final product, a 4-alkyl Neu5Ac chromogenic ketoside or the 7-alkyl Neu5Ac chromogenic ketoside chromogenic ketoside, is obtained, as illustrated in structure [9] for the preferred 4-methyl Neu5Ac chromogenic ketoside ($R_1$=Me and $R_2$=H) or the 7-methyl Neu5Ac methyl ester chromogenic ketoside ($R_1$=H and $R_2$=Me):

[9]

It may be purified, for example, by normal phase and reversed phase chromatography of either the sodium salt form or the free acid, as appropriate. When the 4- or the 7-alkyl group is methyl, the step yield is about 75–80%.

The synthetic strategies yielding the 4-alkyl Neu5Ac chromogenic ketoside or the 7-alkyl Neu5Ac chromogenic ketoside described above represent an unanticipated improvement over the results expected from the state of the art available at the time this invention was made. As noted in U.S. Pat. No. 5,719,020, methylation of the 8,9-ketal protected Neu5Ac methyl ester methyl ketoside by the reactions disclosed therein yielded a mixture of the 4-monomethyl and the 4,7-dimethyl derivatives, with the dimethyl derivative being the minor product. As practiced in U.S. Pat. No. 5,719,020, the mixture is not purified. Instead the mixed chromogenic glycosides are prepared and resolved to give the desired dialkyl derivative only at the stage of this final product. It is pointed out in U.S. Pat. No. 5,719,020 that 4-monoalkyl chromogenic glycosides of Neu5Ac are substrates for mumps neuraminidase and neuraminidases of other viruses.

The examples which follow describe synthetic reactions that may easily be scaled to larger reactions at all stages of the synthetic route, thereby providing larger quantities of the products. From the examples, it is apparent that the methods of the invention provide efficient, economical procedures for the preparation of 4-O-alkyl Neu5Ac chromogenic glycosides or the 7-O-alkyl Neu5Ac chromogenic glycosides on a commercial scale. The purity afforded is high, assuring excellent selectivity for the detection of influenza A and B viruses, and parainfluenza 1, 2, and 3 viruses, while distinguishing from related viruses whose virions also carry neuraminidase activity, as well as from bacterial and mammalian neuraminidase activities which may contaminate a biological sample.

The following examples are presented as particular embodiments of the invention described herein. They are not intended to limit the invention in any way, for the full breadth of the invention is encompassed as described in the present disclosure.

Preparation of 8,9-Isopropylidene Neu5Ac Methyl Ester Methyl Ketoside

EXAMPLE 1

Synthesis of Neu5Ac Methyl Ester Methyl Ketoside

Neu5Ac and Bio-Rad™ cation exchange resin in the acid form (H$^+$) were dried over $P_2O_5$. Neu5Ac (333 g, 1.08 mol) was suspended in 14 L anhydrous methanol. 166.5 g of the acid resin (Bio-Rad™ cation exchange resin(H$^+$)) was added and the mixture was refluxed for 72 h. At this time all the starting material was completely converted to a product with a higher mobility on thin layer chromatography ($R_f$=0.23 in dichloromethane: methanol 80:20). The suspension was filtered and the filtrate was evaporated to dryness. The residue was redissolved in methanol (3.0 L) with heating at 45° C., and the solvent reduced to about 1.0 L under vacuum. The product was crystallized at −20° C. for 24 h. The crystals were collected and washed with cold ethyl acetate-:methanol 6:1 (0.5 L), and dried under vacuum for 15 h. The mother liquor was evaporated to dryness to provide a syrup which was dried under high vacuum for 3–5 h, dissolved in hot methanol (120 mL) and stored at −20° C. for 1 h. Ethyl acetate (380 mL) was added, and the mixture was allowed to crystallize overnight at 0° C. The resulting crystals were collected and dried, and the mother liquor was recycled again to obtain more crystals of the product. The overall yield of Neu5Ac methyl ester methyl ketoside [2] was 232 g (64%).

EXAMPLE 2

One-step Synthesis of 8,9-Isopropylidene Neu5Ac Methyl Ester Methyl Ketoside p-Toluenesulfonic acid monohydrate (14.77 g, 0.078 mol) was added to a stirred solution of Neu5Ac methyl ester methyl ketoside [2] (582 g, 1.72 mol) in anhydrous acetone (9.7 L, dried over 4 Å molecular sieves). The reaction mixture was stirred for 3 h at room temperature, by which time the starting material was completely consumed. The mixture was neutralized with triethylamine (20.0 mL) to reach a pH of about 8–9 (determined using pH paper), and the resulting mixture was evaporated to dryness. To the resulting thick syrup ethyl ether (2.0 L) was added, providing white crystals which were kept at 0° C. for 5 h. After filtering the crystals, the mother liquor was evaporated to dryness, and the residue dissolved in a small amount of dichloromethane. Upon adding diethyl ether an additional crop of crystals was obtained. The total yield of 8,9-isopropylidene Neu5Ac methyl ester methyl ketoside [3] was 600 g (92%).

Preparation of 5-Bromo-3-Indolyl 4-O-Methyl Neu5Ac Ketoside

EXAMPLE 3

Synthesis of 4-O-Methyl 8,9-Isopropylidene Neu5Ac Methyl Ester Methyl Ketoside

Silver oxide (17.61 g, 0.076 mol), freshly prepared by treating silver nitrate with sodium hydroxide, filtering and drying, was added to a suspension of 8,9-isopropylidene Neu5Ac methyl ester methyl ketoside [3] as provided in Example 2 (14.22 g, 0.038 mol) in a mixture of dry dimethylformamide (DMF):toluene 9:1) (180 mL). Dry methyl iodide (7.1 mL, 0.11 mol) was reacted with the mixture at 35° C. for 15 h, by which time all the starting material was completely converted to a major product with a higher mobility ($R_f$=0.50 in chloroform:methanol 9:1). The reaction mixture was diluted with dichloromethane (500 mL), the solids filtered off, and the filtrate was evaporated to dryness. The residue was taken up in dichloromethane:diethyl ether 1:3 and crystallized at 0° C. for 15 h, yielding white crystals. The mother liquor was recycled to provide additional crystals. The overall yield of 4-O-methyl 8,9-isopropylidene Neu5Ac methyl ester methyl ketoside [5] ($R_1$=Me and $R_2$=H) was 12.0 g (81.6%).

EXAMPLE 4

Synthesis of 4-O-Methyl 2,7,8,9-Tetra-O-Acetyl Neu5Ac Methyl Ester

4-O-methyl 8,9-isopropylidene Neu5Ac methyl ester methyl ketoside [5] ($R_1$=Me and $R_2$=H); 8.65 g, 0.022 mol) was suspended in a mixture of methanol and water (1:1 v/v, 80 mL). NaOH (1.0 N, 44.7 mL) was added and the reaction mixture was stirred for 1 h at room temperature. The reaction was neutralized by adding Bio-Rad™ ($H^+$) resin. The resin was filtered off and washed with methanol (500 mL). The washing was combined with the filtrate, and the combined solution was evaporated to dryness. HCl (0.025 M, 150 mL) and Bio-Rad™ ($H^+$) resin (9.0 g) were added to the residue, and the resulting mixture was heated at 70° C. for 16 h. The resin was filtered and washed with water (100 mL). The solvent was evaporated and the residue was dried under high vacuum for 15 h. It was dissolved in dry methanol (250 mL). Bio-Rad™ ($H^+$) resin (9.0 g) was added and the reaction mixture was stirred for 3 h at room temperature. The resin was filtered, pyridine (5.0 mL) was added, and the methanol and the solvents were evaporated. The residue was dried under high vacuum for 15 h over $P_2O_5$. It was then treated with acetic anhydride (20 mL), pyridine (20.0 mL), and dimethylaminopyridine (1.87 g) for 15 h at room temperature. The liquids were evaporated and the residue was purified by chromatography on silica gel. The column was washed with mixtures of hexane and ethyl acetate (2:1, then 1:1), and then the product was eluted with ethyl acetate. After evaporating the ethyl acetate, 4-O-methyl 2,7,8,9-tetraacetate Neu5Ac methyl ester ketoside [6] ($R_1$=Me and $R_2$=Ac; a mixture of the α- and β-anomers) was crystallized by dissolving it in minimal dichloromethane, adding ether (3–5 volumes) and crystallizing at –15° C. for 15 h. Repeated crystallization provided 7.5 g of the product (67%).

EXAMPLE 5

Synthesis of 2-Chloro 4-O-Methyl 7,8,9-Tri-O-Acetyl Neu5Ac Methyl Ester

4-O-methyl 2,7,8,9-tetra-O-acetyl Neu5Ac methyl ester [6] ($R_1$=Me and $R_2$=Ac; 2.0 g, 0.004 mol) was dissolved in anhydrous dichloromethane (40 mL) and cooled to –4 to 0° C. The cooled solution was treated with acetyl chloride (2.0 mL) and a steady stream of anhydrous HCl for 5 h. The solvent was evaporated, and then coevaporated with toluene (100 mL, 3×). The residue was dried under high vacuum for 1 h. The 2-chloro 4-O-methyl 7,8,9-triacetyl Neu5Ac methyl ester [7] ($R_1$=Me and $R_2$=Ac) was dissolved in DMF:tetrahydrofuran (THF) (1:1, 3.0 mL) and dried over 4 Å molecular sieves (1.9 g) for 0.5 h prior to being used in the glycosylation reaction (Example 6).

EXAMPLE 6

Synthesis of 5-Bromo-3-Indolyl 4-O-Methyl 7,8,9-Tri-O-Acetyl Neu5Ac Methyl Ester Ketoside.

5-Bromo-3-indolyl acetate (1.52 g, 0.006 mol) was dissolved in mixed DMF:THF (1:1, v/v, 3.0 mL) at room temperature under nitrogen. The solution was cooled at –10° C. for 20 min and potassium tert-butoxide (786 mg, 0.007 mol) was added. About 1.9 g of the freshly prepared 2-chloro 4-O-methyl 7,8,9-triacetyl Neu5Ac methyl ester M ($R_1$=Me and $R_2$=Ac; Example 5) dissolved in about 6 ml of 1:1 (v/v) DMF/THF solvent was added dropwise to the reaction mixture, and stirred for 15 h at the cooled temperature. The mixture was diluted with dichloromethane (500 mL) and washed with water (100 mL). The aqueous wash was back extracted with dichloromethane (2×250 mL), and the combined organic solutions were treated with acetic anhydride (20 mL) and pyridine (20 mL). The solution was evaporated and the residue was purified by chromatography on silica gel (70–230 mesh) using toluene:acetone (5:1, 3:1, 2:1) as eluents to provide 5-bromo-3-indolyl 4-O-methyl 7,8,9-tri-O-acetyl Neu5Ac methyl ester ketoside [8] ($R_1$=Me and $R_2$=Ac; 1.7 g, 61%) after repeated crystallization from a mixture of dichloromethane-ether. The mother liquor, containing additional product, was treated separately for deprotection in the succeeding step.

EXAMPLE 7

Synthesis of 5-Bromo-3-Indolyl 4-O-Methyl Neu5Ac Ketoside

5-Bromo-3-indolyl 4-O-methyl 7,8,9-tri-O-acetyl Neu5Ac methyl ester ketoside [8] ($R_1$=Me and $R_2$=Ac; 1.5 g, 0.002 mol) was dissolved in sodium methoxide in methanol (5.0 mL) and stirred for 1 h at room temperature. 1.0 M NaOH (5.0 mL) was added and the mixture was stirred for an additional hour. The solution was neutralized with Bio-Rad ($H^+$) resin maintaining the pH at 10.0–10.5. The resin was filtered, and the filtrate was evaporated to dryness. The residue was purified by chromatography on silica gel (70–230 mesh) using dichloromethane:methanol: water:pyridine (80:20:1:1) as eluent to provide the pyridinium salt of 5-bromo-3-indolyl 4-O-methyl Neu5Ac ketoside which was converted into the sodium salt [9] ($R_1$=Me and $R_2$=H) by passage through Bio-Rad AG-50W-X-8 ($Na^+$) ion exchange resin. The sodium salt was lyophilized. The result was applied to a C-18 reverse phase column and washed with water, followed by 5% acetonitrile-water solution. The colorless fractions containing the product were pooled and evaporated under high vacuum at 30° C. to remove most of the acetonitrile. It was then lyophilized, after adjusting the pH to about 10.5–11.0 to provide the final product as a white solid (850 mg, 78.8%). The mother liquor from the previous step (Example 6) was separately treated by these steps to provide additional final product.

Preparation of 5-Bromo-3-Indolyl 7-O-Methyl Neu5Ac Ketoside

EXAMPLE 8

Synthesis of 4-O-Benzyl 8,9-Isopropylidene Neu5Ac Methyl Ester Methyl Ketoside

Benzyl bromide (0.96 mL, 0.008 mol) was added to a mixture of 8,9-isopropylidene Neu5Ac methyl ester methyl ketoside [3] (1.5 g, 0.004 mol) and freshly prepared silver oxide (1.83 g, 0.008 mol) suspended in toluene (30 mL). After 6 h at room temperature, DMF (3 mL) was added and the reaction mixture was heated at 40° C. for 1 day and then quenched with methanol. Filtration and evaporation of the filtrate left a solid which was applied to a column of silica gel using hexane:acetone (2:1) as eluent to provide a modest yield of 4-O-benzyl 8,9-isopropylidene Neu5Ac methyl ester methyl ketoside [5] ($R_1$=Bzl and $R_2$=H) (230 mg, 12%) as a solid.

As an alternative synthetic route, NaH (1.0 g, 0.025 mol) as a 60% dispersion in oil was added in small portions to a solution of 8,9-isopropylidene Neu5Ac methyl ester methyl ketoside [3] (8.0 g, 0.021 mol) in DMF (96 mL) at −10° C. After 0.5 h, benzyl bromide (3.1 mL, 0.026 mol) was added and the reaction mixture was kept at this temperature for 1.5 h. Methanol was added and the solution was evaporated. The residue was chromatographed on silica gel (70–230 mesh) using hexane:acetone (3:1 and 3:2) as eluent. The eluate was evaporated to yield 3.2 g of 4-O-benzyl 8,9-isopropylidene Neu5Ac methyl ester methyl ketoside [5] ($R_1$=Bzl and $R_2$=H) as a white solid (32%). This yield represents almost a three-fold improvement over that obtained using the silver oxide method described above.

EXAMPLE 9

Synthesis of 4-O-Benzyl 7-O-Methyl 8,9-Isopropylidene Neu5Ac Methyl Ester Methyl Ketoside 4-O-benzyl 8,9-isopropylidene Neu5Ac methyl ester methyl ketoside [5] ($R_1$=Bzl and $R_2$=H; 3.2 g, 0.007 mol) was mixed with 4A molecular sieves (4.2 g) in DMF (42 mL) and stirred at room temperature, then barium oxide (3.86 g, 0.025 mol) and barium hydroxide octahydrate (647 mg, 0.002 mol) were added. The mixture was treated with methyl iodide (6.3 mL, 0.1 mol) and kept at room temperature for 2 days. The reaction mixture was then diluted with dichloromethane and filtered through celite and the filtrate washed with 2% aqueous HCl, water, 3% aqueous sodium bisulfate, saturated aqueous sodium bicarbonate, and dried over sodium sulfate. Filtering off the solids and evaporation of the filtrate provided 4-O-benzyl 7-O-methyl 8,9-isopropylidene Neu5Ac methyl ester methyl ketoside [5] ($R_1$=Bzl and $R_2$=Me; 3.2 g, 97%) as a solid.

EXAMPLE 10

Synthesis of 7-O-Methyl 8,9-Isopropylidene Neu5Ac Methyl Ester Methyl Ketoside

4-O-benzyl 7-O-methyl 8,9-isopropylidene Neu5Ac methyl ester methyl ketoside [5] ($R_1$=Bzl and $R_2$=Me; 3.2 g, 0.007 mol) was hydrogenated in methanol (100 mL) in the presence of 5% palladium-on-carbon (4 g) for 3 h. Filtration of the catalyst and evaporation of the solvent provided 7-O-methyl 8,9-isopropylidene Neu5Ac methyl ester methyl ketoside [5] ($R_1$=H and $R_2$=Me; 2.5 g, 96%) as a white solid.

EXAMPLE 11

Synthesis of 7-O-Methyl 2,4,8,9-Tetra-O-Acetyl Neu5Ac Methyl Ester

7-O-methyl 8,9-isopropylidene Neu5Ac methyl ester methyl ketoside [5] ($R_1$=H and $R_2$=Me; 3.2 g, 0.008 mol) was suspended in methanol (80 mL). NaOH (1.0 N, 40 mL) was added and the reaction mixture was stirred for 1 h. The reaction was neutralized by adding Bio-Rad™ (H⁺) resin. The resin was filtered and the filtered solution was evaporated to dryness, providing a white solid (2.9 g). This solid was heated with aqueous HCl (0.025 M, 60 mL) and Bio-Rad™ (H⁺) resin (3.0 g) at 70° C. for 16 h. The resin was filtered, and the filtrate was dried to give 2.35 g of 7-O-methyl Neu5Ac as a solid.

The unpurified compound (1.9 g) and Bio-Rad™ (H⁺) resin (1.5 9) were stirred in anhydrous methanol (50 mL) for 1 h. The resin was removed by filtration and pyridine (2.0 mL) was added to the filtrate. Evaporation provided 7-O-methyl Neu5Ac methyl ester (2.0 g) as a solid. This substance was treated in pyridine (40 mL) with acetic anhydride (20 mL) in the presence of 4-dimethylaminopyridine (150 mg) for 16 h. Evaporation of the reaction mixture and column chromatography of the residue on silica gel (70–230 mesh), using hexane:acetone (4:1, 2:1 and 1:1) as eluents provided 7-O-methyl 2,4,8,9-tetraacetyl Neu5Ac methyl ester [6] ($R_1$=Ac and $R_2$=Me)(2.1 g, 70%) as a foam.

EXAMPLE 12

Synthesis of 7-O-Methyl 2-Chloro 4,8,9-Tri-O-Acetyl Neu5Ac Methyl Ester

7-O-methyl 2,4,8,9-tetraacetyl Neu5Ac methyl ester [6] ($R_1$=Ac and $R_2$=Me)2.1 g, 0.004 mol) was dissolved in anhydrous dichloromethane (36 mL) and cooled to 0° C. Acetyl chloride (1.9 mL, 0.027 mol) was added. After 10 min, HCl gas was bubbled through the mixture for 3.5 h. The solution was then evaporated to provide 7-O-methyl 2-chloro 4,8,9-triacetyl Neu5Ac methyl ester [7] ($R_1$=Ac and $R_2$=Me) as a foam (2.0 g, 100%).

EXAMPLE 12

Synthesis of 5-Bromo-3-Indolyl 7-O-Methyl 4,8,9-Tri-O-Acetyl Neu5Ac Methyl Ester Ketoside Potassium tert-butoxide (0.51 g, 0.005 mol) was added to a suspension of 5-bromo-3-indolyl acetate (1.16 g, 0.005 mol) in DMF:THF (1:1; 5 mL) at 0° C. and stirred at this temperature for 0.5 h. Then a solution of 7-O-methyl 2-chloro 4,8,9-triacetyl Neu5Ac methyl ester [7] ($R_1$=Ac and $R_2$=Me; 1.0 g, 0.002 mol) in DMF:THF (1:1; 6 mL) was added. Stirring was continued for 2 h at 0° C. and for an additional 16 h at 4° C. After evaporation of the solvents from the reaction mixture, the residue was dissolved in dichloromethane. This solution was washed with water and evaporated to dryness. The residue was dissolved in pyridine (20 mL) and acetic anhydride (10 mL) with the addition of dimethylaminopyridine (100 mg) and the mixture was allowed to react for 15 h at room temperature. It was then evaporated, and the product was purified by column chromatography on silica gel (230–400 mesh) using hexane:acetone (6:1, 3:1, and 3:2) as eluent. The eluate was evaporated, providing 5-bromo-3-indolyl 7-O-methyl 4,8,9-triacetyl Neu5Ac methyl ester ketoside [8] ($R_1$=Ac and $R_2$=Me) as a solid (870 mg, 76%).

EXAMPLE 12

Synthesis of 5-Bromo-3-Indolyl 7-O-Methyl Neu5Ac Methyl Ester Ketoside

5-Bromo-3-indolyl 7-O-methyl 4,8,9-triacetyl Neu5Ac methyl ester ketoside [8] ($R_1$=Ac and $R_2$=Me; 600 mg, 0.0009 mol) was treated with sodium methoxide in methanol (8.0 mL). 1.0 M sodium hydroxide (3.5 mL) was added and the mixture was stirred for an additional hour. After neutralizing the mixture with Bio-Rad™ ($H^+$) resin to a pH of ~10–10.5, the product was evaporated and purified by chromatography on silica gel (230–400 mesh) using dichloromethane:methanol:water (90:70:1 and 70:30:3, containing 0.1% pyridine) as eluent. The product was passed through Bio-Rad™ ($Na^+$) resin to provide pure 5-bromo-3-indolyl 7-O-methyl Neu5Ac methyl ester ketoside [9] ($R_1$=H and $R_2$=Me; 380 mg, 82%) as the sodium salt.

We claim:

1. A method of preparing a 4-O-alkyl chromogenic ketoside of N-acetylneuraminic acid (Neu5Ac), said method comprising, in order, the following steps:
    (a) simultaneously alkylating Neu5Ac on its C1 carboxyl and anomeric C2 hydroxyl to provide an alkyl ester alkyl ketoside derivative of Neu5Ac having 4-, 7-, 8-, and 9-hydroxyl groups;
    (b) protecting the 8- and 9-hydroxyl groups of the alkyl ester alkyl ketoside derivative of Neu5Ac to form a protected alkyl ester alkyl ketoside derivative of Neu5Ac;
    (c) alkylating the 4-hydroxyl group of the protected alkyl ester alkyl ketoside derivative of Neu5Ac by contacting the derivative with a composition comprising an alkyl halide to form a 4-O-alkyl protected alkyl ester alkyl ketoside derivative of Neu5Ac;
    (d) selectively deprotecting the 8- and 9-hydroxyl groups and dealkylating the 2-hydroxyl group of the ketoside product obtained in step (c), and derivatizing the resulting 2-, 7-, 8-, and 9-hydroxyl groups;
    (e) activating the anomeric carbon of the product obtained in step (d) to form a 4-O-alkyl alkyl ester derivative of Neu5Ac, derivatized at the 7-, 8- and 9-hydroxyls, and activated at the anomeric carbon;
    (f) contacting the product obtained in step (e) with a suspension of a chromogenic moiety in a solvent to form a chromogenic ketoside of a 4-O-alkyl alkyl ester derivative of Neu5Ac, derivatized at the 7-, 8- and 9-hydroxyls; and
    (g) obtaining a 4-O-alkyl chromogenic ketoside of Neu5Ac from the derivatized chromogenic ketoside obtained in step (f) by cleavage of the derivatized 7-, 8-, and 9-hydroxyls to regenerate the 7-, 8-, and 9-hydroxyl groups.

2. The method described in claim 1 wherein protecting the 8- and 9-hydroxyl groups described in step (b) comprises forming a ketal.

3. The method described in claim 2 wherein the ketal is formed using an acid catalyst chosen from the group consisting of p-toluenesulfonic acid, a salt of p-toluenesulfonic acid, $ZnCl_2$, and $FeCl_3$.

4. The method described in claim 1 wherein protecting the 8- and 9-hydroxyl groups described in step (b) comprises forming an 8,9-epoxide.

5. The method described in claim 1 wherein the alkyl halide employed in step (c) is methyl iodide and the composition further comprises either silver oxide or a mixture of barium oxide and barium hydroxide.

6. The method described in claim 1 wherein activation of the anomeric carbon described in step (e) comprises placing a halo substituent on the anomeric carbon.

7. The method described in claim 6 wherein the halo substituent is chloro.

8. The method described in claim 1 wherein the chromogenic moiety described in step (f) is chosen from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl, a moiety that becomes phosphorescent upon being cleaved from the ketoside, and a moiety that becomes chemiluminescent upon being cleaved from the ketoside.

9. The method described in claim 8 wherein the chromogenic moiety is 5-bromo-3-indolyl.

10. The method described in claim 1 wherein the suspension described in step (f) further comprises a base.

11. The method described in claim 10 wherein the base is chosen from the group consisting of sodium hydroxide, an alkali metal alkoxide, and a mixture of barium oxide and barium hydroxide.

12. The method described in claim 1 wherein the alkyl group on the C1 carboxyl, the alkyl group on the anomeric hydroxyl described in step (a), and the alkyl group at the 4-position of the ketoside derivative of Neu5Ac described in step (c) are the same or different and are chosen from the group consisting of methyl, ethyl, propyl, isopropyl, and normal or branched butyl.

13. The method described in claim 12 wherein the alkyl group on the C1 carboxyl and the alkyl group on the anomeric hydroxyl are methyl.

14. The method described in claim 12 wherein the alkyl group at the 4-position is methyl.

15. A method of preparing a 4-O-methyl chromogenic ketoside of N-acetylneuraminic acid (Neu5Ac), said method comprising, in order, the steps:
    (a) contacting Neu5Ac with methanol and a protonated form of a cation exchange resin to methylate the C1 carboxyl group and the C2 hydroxyl group, forming a methyl ester methyl ketoside of Neu5Ac having 4-, 7-, 8-, and 9-hydroxyl groups;
    (b) contacting the methyl ester methyl ketoside of Neu5Ac with acetone and p-toluenesulfonic acid, to form a 8,9-isopropylidene methyl ester methyl ketoside of Neu5Ac;
    (c) contacting the 8,9-isopropylidene methyl ester methyl ketoside of Neu5Ac with methyl iodide and silver oxide to form a 4-O-methyl 8,9-isopropylidene methylated ester ketoside of Neu5Ac;
    (d) selectively removing the 8,9-isopropylidene and C2 methyl groups from the ketoside product obtained in step (c) and acetylating the anomeric, 7-, 8- and 9-hydroxyl groups of the resulting intermediate;
    (e) activating the anomeric carbon of the product obtained in step (d) by converting the acetate to chloride;
    (f) contacting the activated chloride product provided in step (e) with a suspension of a derivative of 5-bromo-3-indolol and potassium tert-butoxide in a solvent to form a chromogenic ketoside of a 4-O-methyl methyl ester of Neu5Ac, acetylated at the 7-, 8- and 9-hydroxyls; and (g) deblocking the acetyl groups at the 8- and 9-hydroxyl groups and the methyl ester from the chromogenic ketoside of Neu5Ac obtained in step (f), to form the 4-O-methyl chromogenic ketoside of Neu5Ac.

16. A method of preparing a 4-O-methyl chromogenic ketoside of N-acetylneuraminic acid (Neu5Ac), said method comprising, in order, the steps:

(a) contacting Neu5Ac with methanol and a protonated form of a cation exchange resin to methylate the C1 carboxyl group and the C2 hydroxyl group, forming a methyl ester methyl ketoside of Neu5Ac;

(b) contacting the methyl ester methyl ketoside of Neu5Ac with
  (i) an acid chloride of an organic sulfonic acid, and
  (ii) treating the result obtained in step (b) (i) with a composition containing sodium methoxide and methanol, providing an 8,9-epoxide methyl ester methyl ketoside of Neu5Ac having 4-, 7-, 8-, and 9-hydroxyl groups;

(c) methylating the 4-hydroxyl group of the 8,9-epoxide methyl ester methyl ketoside of Neu5Ac by a process chosen from the group consisting of
  (i) contacting the epoxide ketoside with a composition containing methyl iodide and silver oxide,
  (ii) contacting the epoxide ketoside with a composition containing dimethylsulfate and sodium hydride, and
  (iii) a sequential combination of step (c)(i) and step (c)(ii), providing a 4-O-methyl 8,9-epoxide methylated ester ketoside of Neu5Ac;

(d) selectively removing the 8,9-epoxide and C2 methyl groups of the ketoside product obtained in step (c) and acetylating the anomeric, 7-, 8- and 9-hydroxyl groups of the resulting intermediate;

(e) activating the anomeric carbon of the product obtained in step (d) by converting the acetate to chloride;

(f) contacting the activated chloride product provided in step (e) with a suspension of a derivative of 5-bromo-3-indolol and potassium tert-butoxide in a solvent to form a chromogenic ketoside of a 4-O-methyl methyl ester of Neu5Ac, acetylated at the 7-, 8- and 9-hydroxyls; and (g) deblocking the acetyl groups at the 8- and 9-hydroxyl groups and the methyl ester from the chromogenic ketoside of Neu5Ac obtained in step to form the 4-O-methyl chromogenic ketoside of Neu5Ac.

17. A method of preparing a 7-O-alkyl chromogenic ketoside of N-acetylneuraminic acid (Neu5Ac), said method comprising, in order, the steps:

(a) alkylating Neu5Ac on its C1 carboxyl and anomeric C2 hydroxyl to provide an alkyl ester alkyl ketoside derivative of Neu5Ac having 4-, 7-, 8-, and 9-hydroxyl groups;

(b) protecting the 8- and 9-hydroxyl groups of the alkyl ester alkyl ketoside derivative of Neu5Ac to form a protected alkyl ester alkyl ketoside derivative of Neu5Ac;

(c) blocking the 4-hydroxyl group of the protected alkyl ester alkyl ketoside derivative of Neu5Ac with a blocking group to form a blocked protected alkyl ester alkyl ketoside derivative of Neu5Ac;

(d) alkylating the 7-hydroxyl group of the blocked protected alkyl ester alkyl ketoside derivative of Neu5Ac by contacting the derivative with a composition comprising an alkyl halide to form a 7-O-alkyl blocked protected alkyl ester alkyl ketoside derivative of Neu5Ac;

(e) deblocking the 7-O-alkyl blocked protected alkyl ester alkyl ketoside derivative of Neu5Ac to form a 7-O-alkyl protected alkyl ester alkyl ketoside derivative of Neu5Ac;

(f) selectively deprotecting the 8- and 9-hydroxyl groups and dealkylating the 2-hydroxyl group of the ketoside product obtained in step (e), and derivatizing the 2-, 4-, 8-, and 9-hydroxyl groups of the resulting product;

(g) activating the anomeric carbon of the product obtained in step (f) to form a 7-O-alkyl alkyl ester derivative of Neu5Ac, derivatized at the 4-, 8- and 9-hydroxyls, and activated at the anomeric carbon;

(h) contacting the product obtained in step (g) with a suspension of a chromogenic moiety in a solvent to form a chromogenic ketoside of a 7-O-alkyl alkyl ester derivative of Neu5Ac, derivatized at the 4-, 8- and 9-hydroxyls; and (i) obtaining a 7-O-alkyl chromogenic ketoside of Neu5Ac from the derivatized chromogenic ketoside obtained in step (h).

18. The method described in claim 17 wherein protecting the 8- and 9-hydroxyl groups described in step (b) comprises forming a ketal.

19. The method described in claim 18 wherein the ketal is formed using an acid catalyst chosen from the group consisting of p-toluenesulfonic acid, a salt of p-toluenesulfonic acid, $ZnCl_2$, and $FeCl_3$.

20. The method described in claim 17 wherein protecting the 8- and 9-hydroxyl groups described in step (b) comprises forming an 8,9-epoxide.

21. The method described in claim 17 wherein the blocking group in step (c) is benzyl.

22. The method described in claim 17 wherein the alkyl halide employed in step (d) is methyl iodide and the composition further comprises either silver oxide or a mixture of barium oxide and barium hydroxide.

23. The method described in claim 17 wherein activation of the anomeric carbon described in step (g) comprises placing a halo substituent on the anomeric carbon.

24. The method described in claim 23 wherein the halo substituent is chloro.

25. The method described in claim 17 wherein the chromogenic moiety described in step (h) is chosen from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl, a moiety that becomes phosphorescent upon being cleaved from the ketoside, and a moiety that becomes chemiluminescent upon being cleaved from the ketoside.

26. The method described in claim 25 wherein the chromogenic moiety is 5-bromo-3-indolyl.

27. The method described in claim 17 wherein the suspension described in step (h) further comprises a base.

28. The method described in claim 27 wherein the base is chosen from the group consisting of sodium hydroxide, an alkali metal alkoxide, and a mixture of barium oxide and barium hydroxide.

29. The method described in claim 17 wherein the alkyl group on the C1 carboxyl and the alkyl group on the anomeric hydroxyl described in step (a), and the alkyl group at the 7-position of the ketoside derivative of Neu5Ac described in step (d) are the same or different and are chosen from the group consisting of methyl, ethyl, propyl, isopropyl, and normal or branched butyl.

30. The method described in claim 29 wherein the alkyl group on the C1 carboxyl and the alkyl group on the anomeric hydroxyl are methyl.

31. The method described in claim 29 wherein the alkyl group at the 7-position is methyl.

32. A method of preparing a 7-O-methyl chromogenic ketoside of N-acetylneuraminic acid (Neu5Ac), said method comprising, in order, the steps:

(a) contacting Neu5Ac with methanol and a protonated form of a cation exchange resin to methylate the C1 carboxyl group and the C2 hydroxyl group, forming a methyl ester methyl ketoside of Neu5Ac having 4-, 7-, 8-, and 9-hydroxyl groups;

(b) contacting the methyl ester methyl ketoside of Neu5Ac with acetone and p-toluenesulfonic acid, to form an 8,9-isopropylidene methyl ester methyl ketoside of Neu5Ac;

(c) blocking the 4-hydroxyl group of the 8,9-isopropylidene methyl ester methyl ketoside of Neu5Ac with a blocking group to form a blocked 8,9-isopropylidene methyl ester methyl ketoside of Neu5Ac;

(d) contacting the blocked 8,9-isopropylidene methyl ester methyl ketoside of Neu5Ac with methyl iodide and a mixture of barium oxide and barium hydroxide to form a 7-O-methyl blocked 8,9-isopropylidene methyl ester methyl ketoside of Neu5Ac;

(e) deblocking the 7-O-methyl blocked 8,9-isopropylidene methyl ester methyl ketoside of Neu5Ac to form a 7-O-methyl 8,9-isopropylidene methyl ester methyl ketoside of Neu5Ac;

(f) selectively removing the 8,9-isopropylidene and C2 methyl groups from the ketoside product obtained in step (e) and acetylating the anomeric, 7-, 8- and 9-hydroxyl groups of the resulting intermediate;

(g) activating the anomeric carbon of the product obtained in step (f) by converting the acetate to chloride;

(h) contacting the activated chloride product provided in step (g) with a suspension of a derivative of 5-bromo-3-indolol and potassium tert-butoxide in a solvent to form a chromogenic ketoside of a 7-O-methyl methyl ester of Neu5Ac, acetylated at the 7-, 8- and 9-hydroxyls; and (i) deblocking the acetyl groups at the 7-, 8- and 9-hydroxyl groups and the methyl ester from the chromogenic ketoside of Neu5Ac obtained in step (h), to form the 7-O-methyl chromogenic ketoside of Neu5Ac.

33. A method of preparing a 7-O-methyl chromogenic ketoside of N-acetylneuraminic acid (Neu5Ac), said method comprising, in order, the steps:

(a) contacting Neu5Ac with methanol and the protonated form of a cation exchange resin to methylate the C1 carboxyl group and the C2 hydroxyl group, forming a methyl ester methyl ketoside of Neu5Ac having 4-, 7-, 8-, and 9-hydroxyl groups;

(b) contacting the methyl ester methyl ketoside of Neu5Ac with
  (i) an acid chloride of an organic sulfonic acid, and
  (ii) treating the result obtained in step (b) (i) with a composition containing sodium methoxide and methanol, providing an 8,9-epoxide methyl ester methyl ketoside of Neu5Ac;

(c) blocking the 4-hydroxyl group of the 8,9-epoxide methyl ester methyl ketoside of Neu5Ac with a blocking group to form a blocked 8,9-epoxide methyl ester methyl ketoside of Neu5Ac;

(d) methylating the 7-hydroxyl group of the blocked 8,9-epoxide methylated ester ketoside of Neu5Ac provided in step (c) by a process chosen from the group consisting of
  (i) contacting the epoxide ketoside with a composition containing methyl iodide and silver oxide,
  (ii) contacting the epoxide ketoside with a composition containing dimethylsulfate and sodium hydride, and
  (iii) a sequential combination of step (c)(i) and step (c)(ii), providing a 7-O-methyl blocked 8,9-epoxide methylated ester ketoside of Neu5Ac;

(e) deblocking the 7-O-blocked methyl blocked 8,9-epoxide methyl ester methyl ketoside of Neu5Ac to form a 7-O-methyl 8,9-isopropylidene methyl ester methyl ketoside of Neu5Ac;

(f) selectively removing the 8,9-epoxide and C2 methyl groups of the ketoside product obtained in step (e) and acetylating the anomeric, 4-, 8- and 9-hydroxyl groups of the resulting intermediate;

(g) activating the anomeric carbon of the product obtained in step (f) by converting the acetate to chloride;

(h) contacting the activated chloride product provided in step (g) with a suspension of a derivative of 5-bromo-3-indolol and potassium tert-butoxide in a solvent to form a chromogenic ketoside of a 7-O-methyl methyl ester of Neu5Ac, acetylated at the 4-, 8- and 9-hydroxyls; and (i) deblocking the acetyl groups at the 4-, 8- and 9-hydroxyl groups and the methyl ester from the chromogenic ketoside of Neu5Ac obtained in step (h), to form the 7-O-methyl chromogenic ketoside of Neu5Ac.

* * * * *

UNITED STATES PATENT AND TRADEMARK OFFICE
CERTIFICATE OF CORRECTION

PATENT NO.    : 6,420,552 B1
DATED         : July 16, 2002
INVENTOR(S)   : Srivastava et al.

It is certified that error appears in the above-identified patent and that said Letters Patent is hereby corrected as shown below:

Column 23,
Line 47, after "step" insert -- (f), --.

Signed and Sealed this

Twenty-second Day of April, 2003

JAMES E. ROGAN
*Director of the United States Patent and Trademark Office*